United States Patent
Griffus et al.

(10) Patent No.: US 6,804,006 B2
(45) Date of Patent: Oct. 12, 2004

(54) COLOR SAMPLE HOLDER TO ENHANCE REPEATABILITY OF INSTRUMENTAL COLOR READINGS

(75) Inventors: David L. Griffus, Grand Blanc, MI (US); Allan B. Rodrigues, Bloomfield Hills, MI (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 23 days.

(21) Appl. No.: 10/187,544

(22) Filed: Jul. 2, 2002

(65) Prior Publication Data

US 2004/0004718 A1 Jan. 8, 2004

(51) Int. Cl.[7] .......................... G01J 3/46; G01N 21/01
(52) U.S. Cl. .................................... 356/402; 356/244
(58) Field of Search .............................. 356/244, 402; 250/226

(56) References Cited

U.S. PATENT DOCUMENTS

| | | | |
|---|---|---|---|
| 1,971,317 A | | 8/1934 | Sheldon et al. |
| 2,300,695 A | | 11/1942 | Park |
| 4,652,095 A | * | 3/1987 | Mauro ........................ 356/244 |
| 4,652,126 A | * | 3/1987 | Mahooti ...................... 356/244 |
| 4,682,890 A | | 7/1987 | De Macario et al. |
| 5,767,423 A | | 6/1998 | Camp et al. |
| 6,055,050 A | | 4/2000 | Skiffington |
| 6,084,666 A | | 7/2000 | Kindwall et al. |
| 6,186,403 B1 | | 2/2001 | Ozbey et al. |
| 6,198,536 B1 | | 3/2001 | Baker |
| 6,583,879 B1 | * | 6/2003 | Berg et al. .................. 250/226 |

FOREIGN PATENT DOCUMENTS

WO    WO 95/27892    10/1995

OTHER PUBLICATIONS

Rigs & Jigs, catalog from X–Rite, www.X–Rite.com.
Copy of International Search Report (PCT/US 03/20896) dated Jun. 11, 2003.

* cited by examiner

Primary Examiner—F. L. Evans
Assistant Examiner—Kara Geisel
(74) Attorney, Agent, or Firm—Steven C. Benjamin

(57) ABSTRACT

An apparatus for holding a generally flat color sample in a plurality of fixed and repeatable positions in proximity with the optics of a portable color instrument with a uniform and repeatable force. The apparatus has a platform upon which the portable color instrument is secured, a sample stage with multiple index planes upon which a color sample is placed, and a device which urges a pressure foot against the color sample, thereby holding the color sample in position on the stage with a uniform and repeatable force.

31 Claims, 5 Drawing Sheets

COLOR SAMPLE HOLDER TO ENHANCE REPEATABILITY OF INSTRUMENTAL COLOR READINGS

BACKGROUND OF THE INVENTION

The invention is directed to instrumental color readings and in particular to an apparatus that can consistently position a color sample in a plurality of fixed and repeatable positions with a uniform and repeatable force to enhance repeatability of color readings.

The use of portable color measurement instruments, such as spectrophotometers and calorimeters in the automobile manufacturing and automobile refinish paint industry for measuring the color of paint samples is well known.

The shading standards for automotive refinish paints have very close tolerances. The measured color of a sample, however, often varies if the position or angle of a color sample changes slightly in relation to the optics of a portable spectrophotometer. Another problem in the determination of color sample measurements is that the measured color value of a particular color sample may vary from one reading to another if the force with which the color sample and color measurement instrument are held together varies from reading to reading. Because color measurement instrument operators cannot consistently hold the color samples and color measurement instrument together with the same uniform force time after time, the measured colors of samples are subject to operator variability. Thus, different color measurement instrument operators may get different color measurements from the same sample, or an operator may get different measurements from a sample depending on the positioning of the sample with respect to the color measurement instrument optics and the force applied when the color reading is taken.

The color measurement of metallic paints is further complicated by the inherent non-uniformity of metallic finishes. Additionally, because the metallic flakes in metallic paints may be directionally oriented, they are subject to what is known as the "Venetian blind" effect, potentially causing the measured color or metallic paints to vary if the orientation of the sample changes in relation to the color measurement instrument. Because of the inherent non-uniformity and Venetian blind effect, refinish paint manufacturers will take multiple color measurements at different locations on a color sample, all measured with the same sample orientation, and combine those measurements to produce an averaged color measurement.

Variations in color readings caused by differences in the location on a color sample where a color measurement is taken, and the force applied by the color measurement instrument operator from one sample to another, or from one color measurement instrument operator to another for the same sample, may exceed the acceptable tolerances for the sample being measured. Thus, operator variability may produce false rejections or false acceptances of paint formulations. False rejections occur when a color sample that is actually within the acceptable color match tolerances is erroneously rejected. False acceptances occur when a color sample that is actually outside the color match tolerances is erroneously approved. Consistently positioning the color measurement instrument on the same spot on a sample, or for metallic paints on multiple spots, with a uniform and repeatable force is, therefore, essential to obtaining repeatable color readings, and thereby avoid false acceptances and false rejections.

Generally, the optics of a portable color measurement instrument is manually held against the surface of a color sample by the instrument operator. Manual positioning of a color measurement instrument in proximity to a color sample causes variation in color readings because the operator cannot consistently place the color measurement instrument on the sample in the same position and with the same force time after time. It is also generally known that a portable color measurement instrument and test sample can be secured in a fixture to obtain color measurements. Existing fixtures are available for holding a color measurement instrument and color sample but are subject to operator variability because the force with which a color sample is secured in the fixture varies from one operator to another. Moreover, existing holding fixtures do not permit a color measurement instrument operator to make multiple color readings at multiple, repeatable locations on a sample as is required for measuring metallic paint color values.

Automobile manufacturers and refinish paint manufactures experience problems similar to those noted above when using larger stationary color measurement instruments.

The refinish paint industry has a need for an apparatus that can consistently position a color sample in a plurality of fixed and repeatable positions in proximity with the optics port of either a portable or stationary color measurement instrument with uniform and repeatable force, thereby, eliminating color measurement instrument operator variability as a source of error in color readings by refinish paint manufacturing quality control personnel. Benefits accruing from increased repeatability and reproducibility of color measurements include savings from reduced or eliminated remixing of improperly mixed paint, and saving from reduced or eliminated costs of disposal of mixed paint that cannot be remixed.

The invention has the advantage over prior apparatus in that it provides color measurement instrument operators a means for quickly and consistently positioning color samples in multiple distinct and repeatable positions in relation to the optics port of a portable color measurement instrument, and holding the color sample in position with a uniform and repeatable force, thereby eliminating operator variability as a source of error when comparing color samples to known standards, or when measuring samples for future comparison with other samples.

SUMMARY OF THE INVENTION

While this invention can be used with all color measurement instruments, not just spectrophotometers and colorimeters, the invention is now described with reference to calorimeters, as these are the preferred instruments. The present invention is an apparatus for holding a generally flat color sample in juxtaposition with the optics port of a calorimeter, comprising a calorimeter support plate, a color sample stage defining an aperture capable of receiving the colorimeter optics shoe; a means for removably securing the colorimeter support plate to the calorimeter with the optics shoe engaged in the aperture; a means for positioning the color sample in a plurality of fixed and repeatable positions on the color sample stage wherein the optics port is disposed on a distinct location on the color sample in each of the positions, and the aperture is fully covered by the color sample in all positions; and a means for removably securing the color sample to the color sample stage with a uniform and repeatable force.

DETAILED DESCRIPTION

Figure 1:
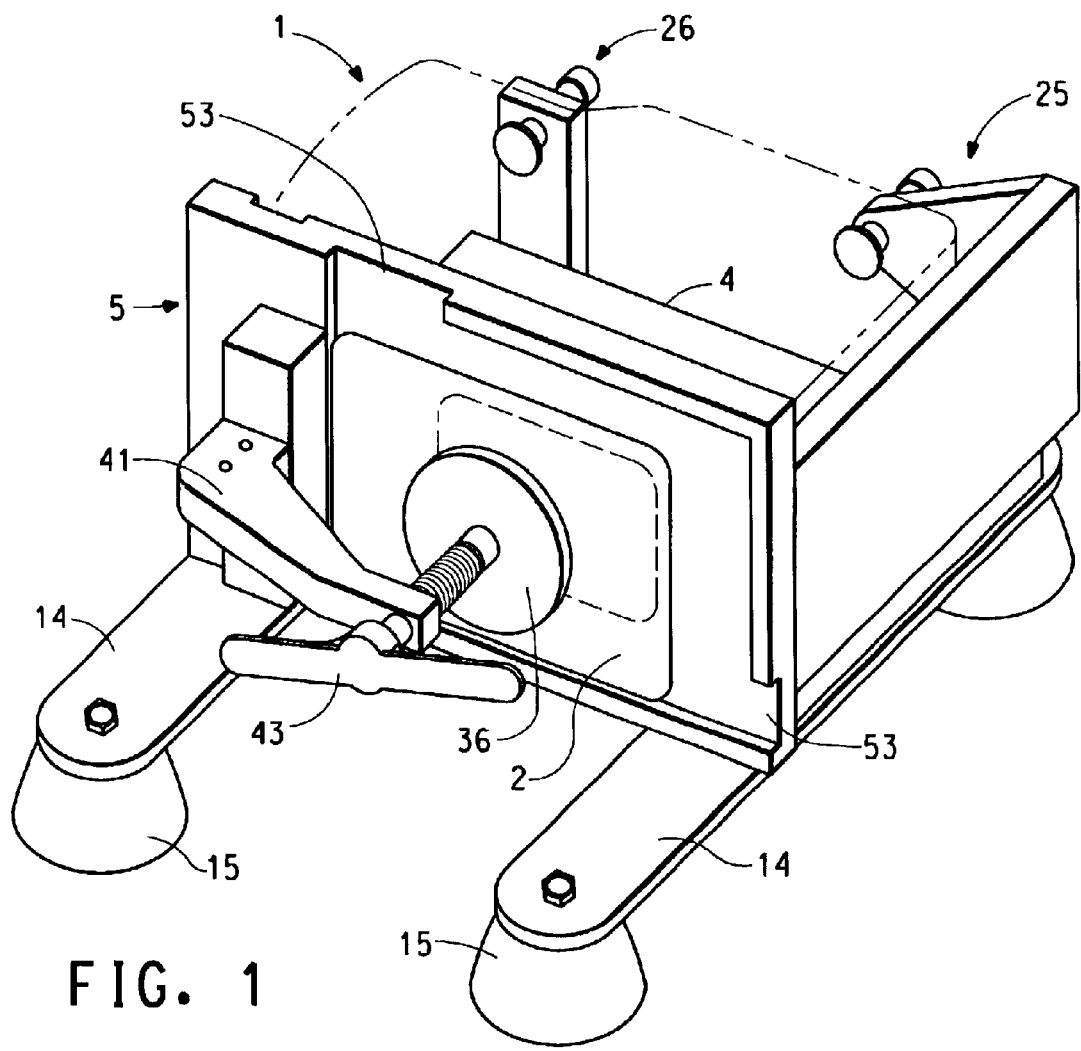
FIG. 1 is an isometric view of the assembled invention showing the sample stage, the colorimeter platform, and the pressure plate in a raised position.
Figure 2:
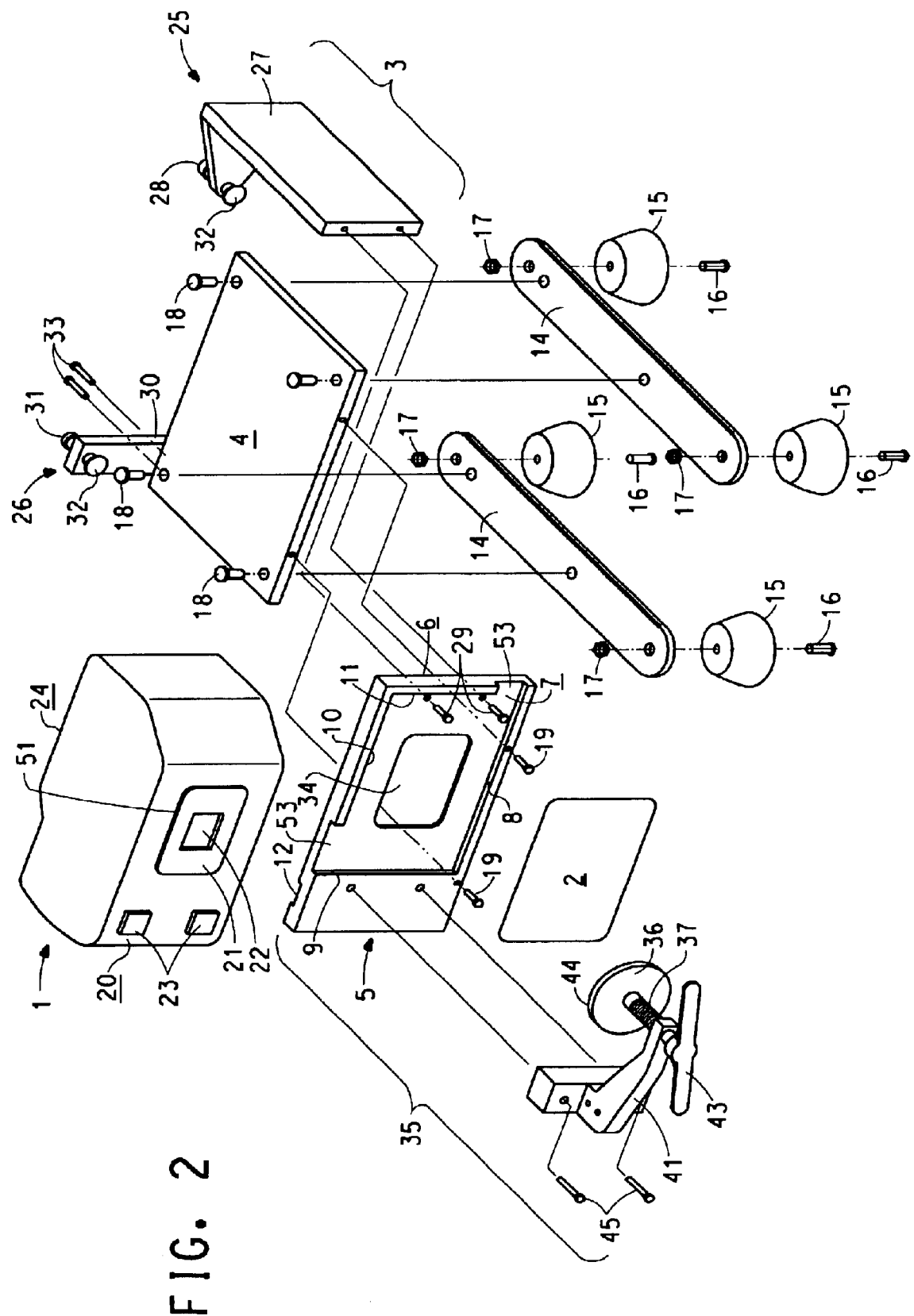
FIG. 2 is an explode isometric drawing of the invention.

A calorimeter and color sample holder constructed in accordance with a preferred embodiment of the present invention is illustrated in FIGS. 1 and 2. The portable colorimeter (1), as is generally known within the art, includes a colorimeter bottom surface (20); a colorimeter optics shoe (21) having a plane surface, an optics port (22) through which light travels to the calorimeter optics, and a projection (51) from the calorimeter bottom surface (20); at least one calorimeter foot (23); and a calorimeter top surface (24).

As illustrated in FIG. 2, the invention comprises a colorimeter holding assembly (3) and a color sample holding assembly (35). The colorimeter holding assembly (3) comprises a base plate (4), a colorimeter support plate (5), a first holding arm (25) and a second holding arm (26). The colorimeter support plate (5) comprises a colorimeter mounting surface (6), an aperture (34), a colorimeter foot receiving groove (12), a color sample stage (7), and a first, second, third and fourth color sample index plane (8, 9 10, & 11).

FIG. 2 also shows the base plate (4) supported by two base support members (14) and four feet (15), however, any arrangement of support members and feet which provides sufficient stability to operate the colorimeter may be used. The base support member (14), for example, may be a single plate or multiple plates, and the number of feet (15) may, for example, be two elongated feet, or three or more small feet. The base support members (14) are preferably a light weight metal such as aluminum, however, any known material capable of providing the necessary strength and stability may be used. The feet (15) are preferably an elastomeric material with high coefficient of friction with a table or other working surface, thereby preventing unintended movement of the holder. The feet (15) are rigidly attached to the base support members (14) by an attachment means such as screws (16) and nuts (17). The base plate (4) is rigidly attached to the base support members (14) by an attachment means such as screws (18).

The calorimeter support plate (5) is rigidly and perpendicularly attached to the base plate (4) by an attachment means such as screws (19). The base plate (4) and colorimeter support plate (5) are preferably a lightweight metal such as aluminum with a smooth machined surface, however, any material capable of providing the necessary rigidity, strength and stability may be used.

The calorimeter (1) is removably held in contact with the colorimeter mounting surface (6) by a holding means. FIG. 1, for example, shows a first holding arm (25), and a second holding arm (26). As shown in FIG. 2, the first holding arm (25) comprises a first holding arm body (27), and a first holding screw (28). The first holding arm body (27) is rigidly attached to the colorimeter support plate (5), by an attachment means such as screws (29), and extends from the mounting surface (6) beyond the calorimeter top surface (24) and extends around the calorimeter top surface (24) a sufficient distance to permit a holding means, for example the first holding screw (28), to engage the colorimeter top surface (24). FIG. 2 also shows a second holding arm (26) comprising a second holding arm body (30) and a second holding means, for example a second holding screw (31). The second holding arm body (30) is rigidly attached to the base plate (4) by an attachment means such as screws (33), and extends from the base plate (4) a sufficient distance to permit the second holding screw (31) to engage the colorimeter top surface (24). The invention illustrated in the figures, includes first and second holding screws, (28) and (31), having holding screw pads (32), which prevent marring of the calorimeter top surface (24) when the calorimeter holding screws (28 & 31) are tightened against the colorimeter top surface (24). The first holding arm body (27) and second holding arm body (30) are preferably a lightweight metal such as aluminum with a smooth machined surface, however, any material providing sufficient rigidity and strength may be used. The pads (32) are preferably a plastic or elastomeric material, but any material which will not mar the colorimeter surface (24) may be used.

While the invention as illustrated in FIGS. 1 and 2 shows the portable colorimeter (1) held in place by means of the first and second holding arms (25 & 26), and first and second holding screws (28 & 31), other means for removably but rigidly holding the calorimeter optics shoe (21) engaged in the aperture (34) such as elastic or inelastic straps or bands which wrap around the colorimeter (2), or by means of springs urging the holding screw pads (32) against the calorimeter top surface (24) are also suitable.

The color sample holding assembly (35) comprises the color sample stage (7), which is part of the calorimeter support plate (5), and a means for removably holding the color sample (2) in a plurality of fixed and repeatable positions on the color sample stage (7).

As shown in FIG. 2, the color sample stage (7) comprises a plane surface with a width defined by a first and a third color sample index plane (8 & 10); and a length defined by a second and a fourth color sample index plane (9 & 11). The aperture (34) for receiving the colorimeter optics shoe (21) of a portable colorimeter (1), is located in substantially the center of the color sample stage (7). FIG. 2 shows the four color sample index planes (8, 9, 10 and 11) as plane surfaces intersecting and substantially perpendicular to the color sample stage (7), and extending a sufficient distance from the plane of the color sample stage (7) that the colorimeter operator can easily place the color sample (2) on the color sample stage (7), and slide the color sample (2) into contact with the appropriate adjacent color sample indexes for multiple color measurements of a single sample (2). FIGS.

Figure 1A:
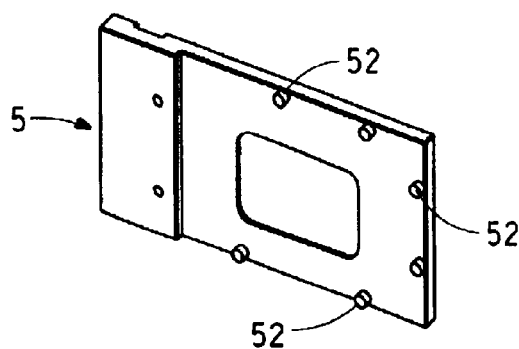
FIG. 1A shows an alternative configuration of the color sample stage using multiple pins (52) to define the index surfaces used to repeatably position the color sample on the color sample stage.

1 and 2 also show sample removal notches (53) in the third and fourth color sample index planes 10 & 11) to facilitate removal of the color sample (2) from the color sample stage (7). An alternative embodiment of the color sample index planes is shown in FIG. 1A. In this figure, the color sample index planes are defined by multiple protrusions (52) which define the index planes. These protrusions may be machined from the material forming the color sample stage (7), or separately manufactured and attached.

The first color sample index plane (8) is substantially perpendicular to the second color sample index plane (9); and the third color sample index plane (10) is substantially perpendicular to the fourth color sample index plane (11). The third color sample index plane (10) is preferably substantially parallel to the first color sample index plane (8), and the fourth color sample index plane (11) is preferably substantially parallel to the second color sample index plane (9), so that this means for positioning the sample is a substantially rectangular perimeter.

The width and length of the color sample stage (7), as defined by the color sample planes (8, 9, 10 & 11), is larger than the corresponding width and length of the color sample (2). The calorimeter optics port (22), therefore, is disposed on completely different locations on the color sample (2) when the color sample (2) is in linear contact with any two adjacent color sample index planes as shown in FIGS. 4, 5, 6 and 7. The width and length of the color sample stage (7) is also small enough that the color sample (2) fully covers the aperture (34) when the color sample (2) is in substantial linear contact with any two adjacent color sample index planes.

The aperture (34) is substantially the same size and shape as the calorimeter optics shoe (21), and receives the colorimeter optics shoe (21). The aperture (34) and the colorimeter foot receiving groove (12) are positioned to receive the colorimeter optics shoe (21) and the calorimeter feet (23) when the calorimeter is secured in place in the calorimeter holding assembly (3).

When the portable calorimeter (1) is secured in the calorimeter support assembly (3) the plane surface of the color sample stage (7) is substantially coincident with the plane surface of the calorimeter optics shoe (21). A generally flat color sample (2) secured on the color sample stage (7) will, therefore, be in substantial contact with both the color sample stage (7) and the calorimeter optics shoe (21).

Figure 4:
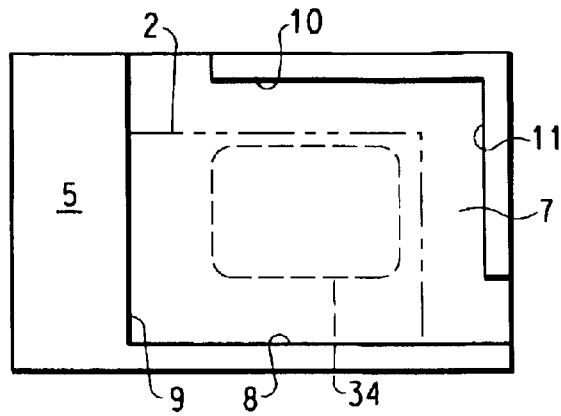
FIG. 4 is a front view of the colorimeter support plate (5), showing the color sample stage (7) and the color sample (2) in juxtaposition with the first and second color sample index planes (8 & 9)
Figure 5:
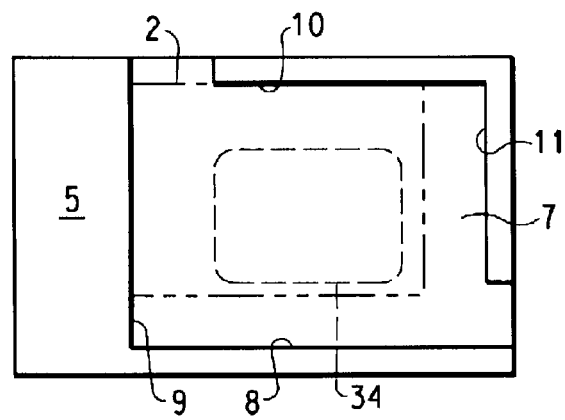
FIG. 5 is a front view of the calorimeter support plate (5), showing the color sample stage (7) and the color sample (2) in juxtaposition with the second and third color sample index planes (9 & 10).
Figure 6:
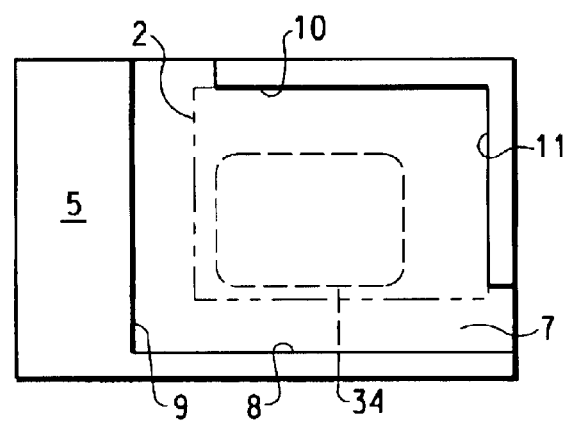
FIG. 6 is a front view of the colorimeter support plate (5), showing the color sample stage (7) and the color sample (2) in juxtaposition with the third and fourth color sample index planes (10 & 11).
Figure 7:
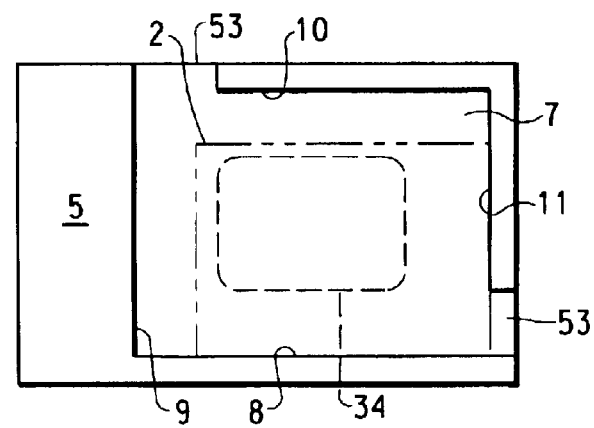
FIG. 7 is a front view of the colorimeter support plate (5), showing the color sample stage (7) and the color sample (2) in juxtaposition with the first and fourth sample index planes (8 & 11).

As illustrated in FIGS. 4 through 7, the calorimeter operator can consistently take color measurements at four distinct and repeatable locations on the color sample (2) by placing the color sample (2) on the color sample stage (7), and moving the color sample into contact with any two adjacent index planes, for example with the first and second color sample index planes (8 & 9), see FIG. 4, the second and third color sample index planes (9 & 10), see FIG. 5 the third and fourth color sample index planes (10 & 11), see FIG. 6, and the first and fourth color sample index planes (8 & 11), see FIG. 7.

Figure 3:
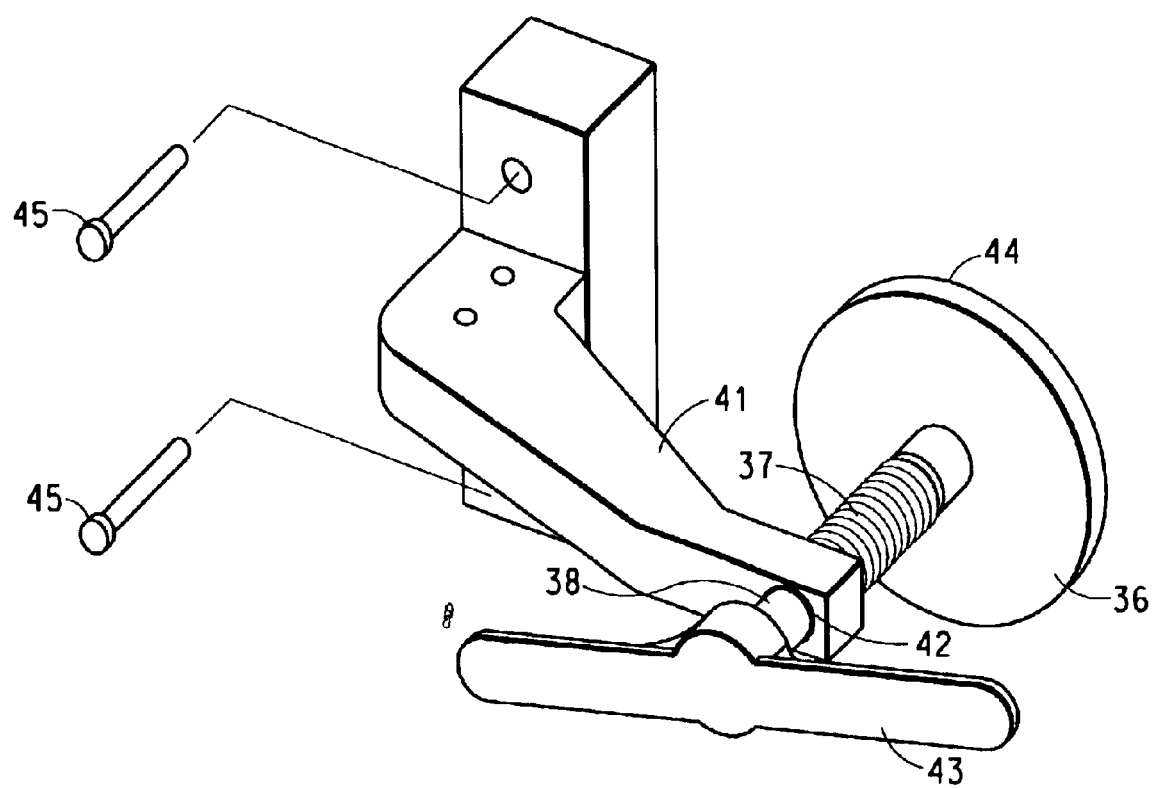
FIG. 3 is an isometric view of the sample holder.

As shown in FIGS. 2 and 3, the means for removably holding the color sample on the color sample stage (7) preferably comprises; a support arm (41) rigidly attached to the calorimeter support plate (5) by an attachment means such as screws (45); a cylindrical journal (42) rigidly supported by the support arm (41); a cylindrical shaft (38), slidably engaged in the cylindrical journal (42); a pressure foot (36) comprising a plane surface (44), rigidly or flexibly attached to the cylindrical shaft (38); a handle (43) fixedly attached to the handle end of the cylindrical shaft (38), and a means for urging the pressure foot (36) against the color sample (2) or the color sample stage (7), such as a helical compression spring (37) coaxially mounted compressed on the cylindrical shaft (38) between the pressure foot (36) and the cylindrical journal (42). The dimensions of the pressure foot surface in contact with the color sample are preferably at least a large as the optics port (22) of the colorimeter (1). The pressure foot (36) is preferably a lightweight metal such as aluminum with a smooth machined surface, however, any material providing the necessary strength and rigidity may be used. The support arm (41) and handle (43) are preferably a lightweight metal such as aluminum, however, any material, which provides sufficient strength and rigidity, may be used. The cylindrical shaft (38), and cylindrical journal (42) are preferably metal, however, any material providing sufficient strength and rigidity, and which permits the cylindrical shaft (38) to slide within the cylindrical journal (42) may be used.

The cylindrical shaft (38), FIGS. 2 and 3, is of sufficient length, and the compression spring of sufficient relaxed and compressed length and the spring coefficient of the spring compression means of sufficient force to hold the color sample (2) in the desired position on the sample stage (7) without operator intervention. By pulling on the handle (43), the calorimeter operator can disengage the pressure foot (36) from the color sample (2) to remove the sample (2) from the color sample stage (7), or from the color sample stage (7), to place the color sample (2) on the color sample stage (7).

While the motive force holding the color sample (2) against the color sample stage (7) in the preferred embodiment of the invention is a helical compression spring (37), other means for urging the pressure foot (36) against the color sample stage (7) with a uniform and repeatable force are also suitable. Examples of alternative motive forces include, but are not limited to, other types or configurations of springs, electric solenoids, or pneumatic or hydraulic cylinders. Because of the complexity, cost and weight imposed by these alternative means for actuating the pressure foot (36) on the invention, these examples are not preferred.

To facilitate placement of the color sample (2) on the color sample stage (7), the cylindrical shaft (38) optionally includes a means for securing the pressure foot (36) in a raised position whereby the pressure foot (36) is not in contact with the color sample (2), the color sample stage (7) or the calorimeter optics shoe (21). Means to secure the pressure foot (36) in a raised position, sometimes referred to as a "camlock", are known to those skilled in the art.

FIGS. 1 and 2 show the portable colorimeter (1) in a horizontal position, and the color sample (2) in a vertical position, the spatial orientation of the invention, however, is not significant, and the invention will work in any orientation. An alternative orientation for example includes holding the colorimeter in a position whereby the colorimeter optics port (21) is facing up, and the color sample stage (7) and color sample (2) are horizontal. The orientation as shown in the figures is preferred because it facilitates placement and removal of color samples (2) on the color sample stage (7), and reduces the likelihood that dirt or dust will settle on the calorimeter optics port (21).

The invention will accommodate any conventional color samples used by automobile manufacturers and the refinish paint industry. FIGS. 1 and 2 show the invention constructed to hold a particular model and brand hand held colorimeter (1), the invention will also work, however, with other brands and models of hand held calorimeters and spectrophotometers when constructed with appropriate dimensions to accommodate the dimensions and configurations of specific calorimeter and spectrophotometer models.

Figure 2A:
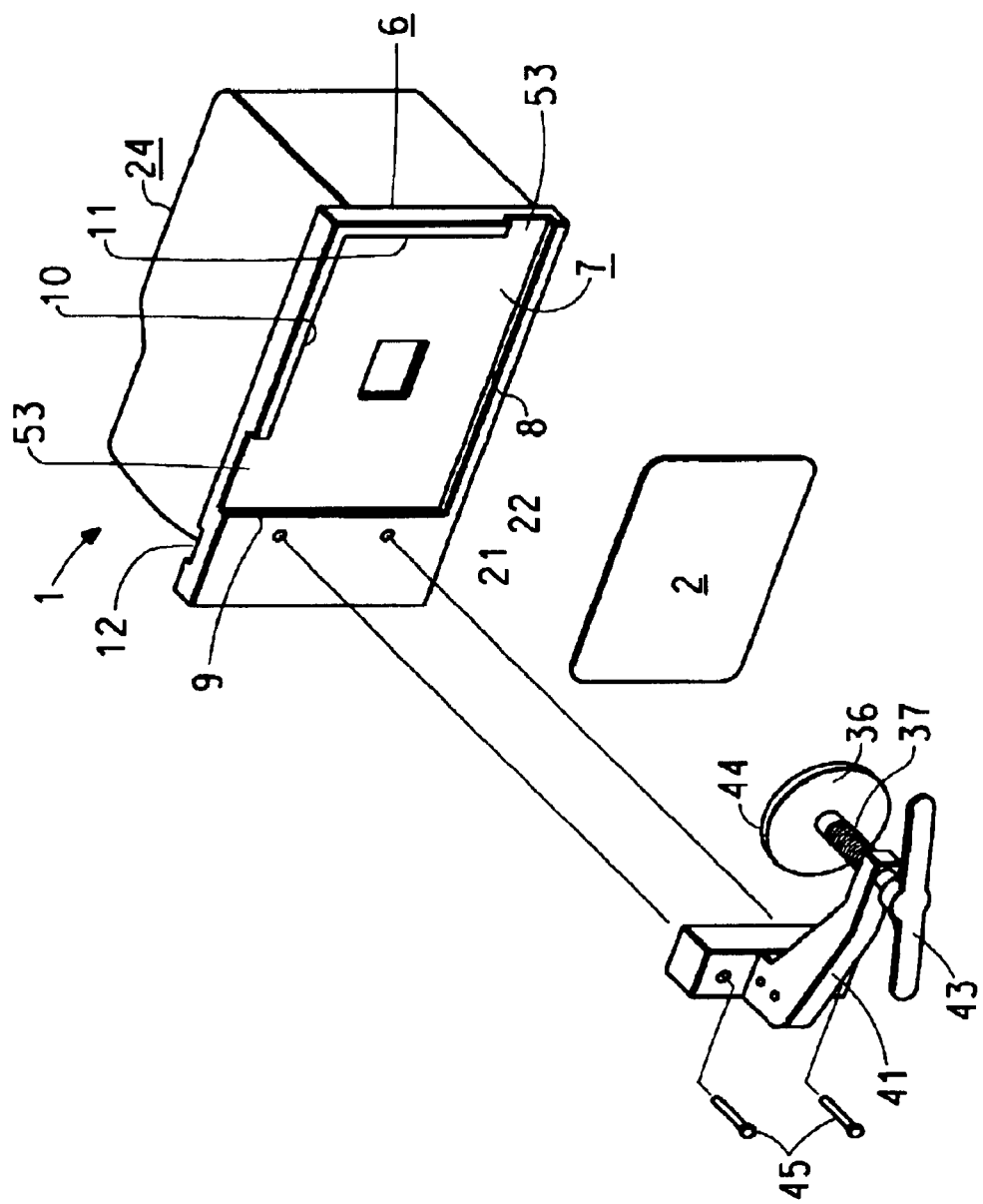
FIG. 2A is exploded isometric drawing of the invention constructed as an integral part of a calorimeter, which may be of either the stationary or portable type.

The invention will also accommodate stationary calorimeters and spectrophotometers by changing the means for holding the colorimeter mounting surface (6) in contact with the calorimeter or spectrophotometer from holding arms (25) and (26) as shown in FIGS. 1 and 2, to an alternative means for removably holding the color sample holding assembly (35) in rigid contact with the colorimeter for example by means of screws, and can also be permanently attached, or included as an integral, and non-removable, part of either a portable or stationary calorimeter or spectrophotometer as shown in FIG. 2A.

What is claimed is:

1. An apparatus for holding a portable color measurement instrument comprising an optics port with a geometric center, and a color sample, said apparatus comprising:
   a) a color measurement instrument support plate comprising a color measurement instrument support surface, a color sample stage, and defining an aperture substantially aligned with said geometric center of said optics port;
   b) a means for removably securing said portable color measurement instrument to said color measurement instrument support surface with said optics port substantially aligned with said aperture;
   c) a means for positioning said color sample in a plurality of fixed and repeatable positions on said color sample stage wherein said optics port is disposed on a distinct location on said color sample in each of said positions, and said aperture is fully covered by said color sample in all positions; and
   d) a means for removably securing said color sample to said color sample stage with a uniform and repeatable force;
wherein said color measurement instrument further comprises a color measurement instrument optics shoe comprising a plane surface; and said color sample stage further comprises a plane surface substantially coincident with said plane surface of said color measurement instrument optics shoe when said optics shoe is engaged in said aperture.

2. The apparatus of claim 1 wherein said color measurement instrument further comprises a top surface, and said means for removably securing said color measurement instrument to said color measurement instrument support surface further comprises;
   a) a base plate rigidly and perpendicularly affixed to said color instrument support plate;
   b) a first holding arm rigidly affixed to said base plate;
   c) and a second holding arm rigidly affixed to said color measurement instrument support plate;
   d) said first support arm further comprising a first holding screw disposed on said top surface of said color measurement instrument;
   e) said second support arm further comprising a second holding screw disposed on said top surface of said color measurement instrument.

3. The apparatus of claim 2 wherein said means for positioning said color sample comprises a substantially rectangular perimeter of said color sample stage defined by:
   a) a first color sample index plane rigidly affixed to said color sample stage, and substantially perpendicular to said color sample stage;
   b) a second sample index plane rigidly affixed to said color sample stage, and substantially perpendicular to said color sample stage, and substantially perpendicular to said first color sample index plane;
   c) a third color sample index plane rigidly affixed to said color sample stage, and substantially perpendicular to said color sample stage, and substantially perpendicular to said second color sample index plane;
   d) fourth color sample index plane rigidly affixed to said color sample stage, and substantially perpendicular to said third color sample index plane, and substantially perpendicular to said first color sample index plane;
   e) said aperture being between said first and third color sample index planes, and between said second and fourth color sample index planes in a position such that said color measurement instrument optics port is disposed on a distinct location on said color sample when said color sample is in juxtaposition with said first and second color sample index planes, said second and third color sample index planes, said third and fourth color sample index planes and said first and fourth color sample index planes; and
   f) said aperture being also located on said color sample stage such that said aperture is fully disposed on said color sample when said color sample is in juxtaposition with any pair of adjacent color sample index planes.

4. The apparatus of claim 3 wherein said means for removably securing said color sample to said color sample stage comprises a compression means.

5. The apparatus of claim 4 wherein said means for removably securing said color sample to said color sample stage comprises a helical compression spring.

6. The apparatus of claim 3 wherein said means for removably securing said color sample to said color sample stage comprises:
   a) a support arm fixedly attached to said base plate;
   b) a cylindrical journal fixedly attached to said support arm;
   c) a cylindrical shaft slidably engaged in said cylindrical journal; said cylindrical shaft having a pressure foot end; and an axis substantially perpendicular to said plane of said color sample stage, and substantially coincident with said geometric center of said optics part;
   d) a pressure foot fixedly attached to said pressure foot end;
   e) a helical compression spring coaxially mounted on said shaft between said cylindrical journal and said pressure foot; and
   f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

7. The apparatus of claim 3 wherein said means for securing said color sample to said color sample stage comprises:
   a) a support arm fixedly attached to said base plate;
   b) a cylindrical journal fixedly attached to said support arm;
   c) a cylindrical shaft slidably engaged in said cylindrical journal; said cylindrical shaft having a pressure foot end; and an axis substantially perpendicular to said plane of said color sample stage, and substantially coincident with said geometric center of said optics port;

d) a pressure foot flexibly attached to said pressure foot end; and e) a helical compression spring coaxially mounted on said shaft between said cylindrical journal and said pressure foot;

f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

8. The apparatus of claim 6 wherein said means for securing said color sample to said color sample stage further comprises a means to secure said pressure foot in a position not engaged with said color sample stage.

9. The apparatus of claim 7 wherein said means for securing said color sample to said color sample stage further comprises a means to secure said pressure foot in a position not engaged with said color sample stage.

10. The apparatus of claim 2, wherein said means for removably securing said color sample to said color sample stage comprises a compression means.

11. The apparatus of claim 2 wherein said means for removably securing said color sample to said color sample stage comprises a helical compression spring.

12. The apparatus of claim 2 wherein said means for removably securing said color sample to said color sample stage comprises:

a) a support arm fixedly attached to said base plate;

b) a cylindrical journal fixedly attached to said support arm;

c) a cylindrical shaft slidably engaged in said cylindrical journal; said cylindrical shaft having a pressure foot end; and an axis substantially perpendicular to said plane of said color sample stage, and substantially coincident with said geometric center of said optics port;

d) a pressure foot fixedly attached to said pressure foot end;

e) a helical compression spring coaxially mounted on said shaft between said cylindrical journal and said pressure foot; and f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

13. The apparatus of claim 2 wherein said means for securing said color sample to said color sample stage comprises:

a) a support arm fixedly attached to said base plate;

b) a cylindrical journal fixedly attached to said support arm;

c) a cylindrical shaft slidably engaged in said cylindrical journal; said, cylindrical shaft having a pressure foot end; and an axis substantially perpendicular to said plane of said color sample stage, and substantially coincident with said geometric center of said optics port;

d) a pressure foot flexibly attached to said pressure foot end; and e) a helical compression spring coaxially mounted on said shaft between said cylindrical journal and said pressure foot;

f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

14. The apparatus of claim 12 wherein said means for securing said color sample to said color sample stage further comprises a means to secure said pressure foot in a position not engaged with said color sample stage.

15. The apparatus of claim 13 wherein said means for securing said color sample to said color sample stage further comprises a means to secure said pressure foot in a position not engaged with said color sample stage.

16. The apparatus of claim 1 wherein said means for removably securing said color sample to said color sample stage comprises a compression means.

17. The apparatus of claim 1 wherein said means for removably securing said color sample to said color sample stage comprises a helical compression spring.

18. The apparatus of claim 1 wherein said means for removably securing said color sample to said color sample stage comprises:

a) a support arm fixedly attached to said base plate;

b) a cylindrical journal fixedly attached to said support arm;

c) a cylindrical shaft slidably engaged in said cylindrical journal; said cylindrical shaft having a pressure foot end; and an axis substantially perpendicular to said plane of said color sample stage, and substantially coincident with said geometric center of said optics port;

d) a pressure foot fixedly attached to said pressure foot end;

e) a helical compression spring coaxially mounted on said shaft between said cylindrical journal and said pressure foot; and f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

19. The apparatus of claim 1 wherein said means for securing said color sample to said color sample stage comprises:

a) a support arm fixedly attached to said base plate;
b) a cylindrical journal fixedly attached to said support arm;
c) a cylindrical shaft slidably engaged in said cylindrical journal: said cylindrical shaft having a pressure foot end; and an axis substantially perpendicular to said plane of said color sample stage, and substantially coincident with said geometric center of said optics port;
d) a pressure foot flexibly attached to said pressure foot end;
e) a helical compression spring coaxially mounted on said shaft between said cylindrical journal and said pressure foot; and
f) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

20. The apparatus of claim 18 wherein said means for securing said color sample to said color sample stage further comprises a means to secure said pressure foot in a position not engaged with said color sample stage.

21. The apparatus of claim 19 wherein said means for securing said color sample to said color sample stage further comprises a means to secure said pressure foot in a position not engaged with said color sample stage.

22. An apparatus for holding a portable color measurement instrument comprising an optics port with a geometric center, and a color sample, said apparatus comprising:
   a) a color measurement instrument support plate comprising a color measurement instrument support surface, a color sample stage, and defining an aperture substantially aligned with said geometric center of said optics port;
   b) a means for removably securing said portable color measurement instrument to said color measurement instrument support surface with said optics port substantially aligned with said aperture;
   c) a means for positioning said color sample in a plurality of fixed and repeatable positions on said color sample stage wherein said optics port is disposed on a distinct location on said color sample in each of said positions, and said aperture is fully covered by said color sample in all positions; and
   d) a means for removably securing said color sample to said color sample stage with a uniform and repeatable force;
wherein said means for removably securing said color sample to said color sample stage comprises a helical compression spring.

23. An apparatus for holding a portable color measurement instrument comprising an optics port with a geometric center, and a color sample, said apparatus comprising:
   a) a color measurement instrument support plate comprising a color measurement instrument support surface, a color sample stage, and defining an aperture substantially aligned with said geometric center of said optics port;
   b) a means for removably securing said portable color measurement instrument to said color measurement instrument support surface with said optics port substantially aligned with said aperture;
   c) a means for positioning said color sample in a plurality of fixed and repeatable positions on said color sample stage wherein said optics port is disposed on a distinct location on said color sample in each of said positions, and said aperture is fully covered by said color sample in all positions; and
   d) a means for removably securing said color sample to said color sample stage with a uniform and repeatable force;
wherein said means for removably securing said color sample to said color sample stage comprises:
   d.1) a support arm fixedly attached to said base plate;
   d.2) a cylindrical journal fixedly attached to said support arm;
   d.3) a cylindrical shaft slidably engaged in said cylindrical journal; said cylindrical shaft having a pressure foot end; and an axis substantially perpendicular to said plane of said color sample stage, and substantially coincident with said geometric center of said optics port;
   d.4) a pressure foot fixedly attached to said pressure foot end;
   d.5) a helical compression spring coaxially mounted on said shaft between said cylindrical journal and said pressure foot; and
   d.6) said helical compression spring having a relaxed length sufficiently long, and a spring coefficient sufficiently large; to urge said pressure foot against said color sample stage with sufficient force to hold said color sample in a fixed position on said color sample stage; and a compressed length sufficiently short to permit said pressure foot to be disengaged from said color sample stage a distance sufficient to permit placement and removal of said color sample on said color sample stage.

24. The apparatus of claim 23 wherein said means for securing said color sample to said color sample stage further comprises a means to secure said pressure foot in a position not engaged with said color sample stage.

25. The apparatus of claim 1, 22 or 23 wherein said color measurement instrument is a portable colorimeter.

26. An apparatus for holding a portable color measurement instrument comprising an optics port with a geometric center, and a color sample, said apparatus comprising:
   a) a color measurement instrument support plate comprising a color measurement instrument support surface, a color sample stage, and defining an aperture substantially aligned with said geometric center of said optics port;
   b) a means for removably securing said portable color measurement instrument to said color measurement instrument support surface with said optics port substantially aligned with said aperture;
   c) a means for positioning said color sample in a plurality of fixed and repeatable positions on said color sample stage wherein said optics part is disposed on a distinct location on said color sample in each of said positions, and said aperture is fully covered by said color sample in all positions; and
   d) a means for removably securing said color sample to said color sample stage with a uniform and repeatable force;

wherein said means for securing said color sample to said color sample stage comprises:

d.1) a support arm fixedly attached to said base plate;

d.2) a cylindrical journal fixedly attached to said support arm;

d.3) a cylindrical shaft slidably engaged in said cylindrical journal; said cylindrical shaft having a pressure foot end; and an axis substantially perpendicular to said plane of said color sample stage, and substantially coincident with said geometric center of said optics port;

d.4) a pressure foot flexibly attached to said pressure foot end; and d.5) a helical compression spring coaxially mounted on said shaft between said cylindrical journal and said pressure foot;

d.6) said helical compression spring having a relaxed length sufficiently long, and a spring coefficient sufficiently large; to urge said pressure foot against said color sample stage with sufficient force to hold said color>sample in a fixed position on said color sample stage; and a compressed length sufficiently short to permit said pressure foot to be disengaged from said color sample stage a distance sufficient to permit placement and removal of said color sample on said color sample stage.

27. The apparatus of claim 26 wherein said means for securing said color sample to said color sample stage further comprises a means to secure said pressure foot in a position not engaged with said color sample stage.

28. An apparatus for holding a color sample in juxtaposition with the optics port of a color measurement instrument comprising:

a) a color sample stage fixedly attached to said color measurement instrument, said color sample stage defining an aperture coaxially aligned with said optics port of said color measurement instrument, and said optics port comprises a geometric center;

b) a means for positioning said color sample in a plurality of fixed and repeatable positions on said color sample stage wherein said optics port is disposed on a distinct location on said color sample in each of said positions, and said optics port is fully covered by said color sample in all positions;

wherein said means for positioning said color sample further comprises a substantially rectangular perimeter of said color sample stage defined by;

b.1) a first color sample index plane rigidly affixed to said color sample stage, and substantially perpendicular to said color sample stage;

b.2) a second sample index plane rigidly affixed to said color sample stage, and substantially perpendicular to said color sample stage, and substantially perpendicular to said first color sample index plane, b.3) a third color sample index plane rigidly affixed to said color sample stage, and substantially perpendicular to said color sample stage, and substantially perpendicular to said second color sample index plane;

b.4) fourth color sample index plane rigidly affixed to said color sample stage, and substantially perpendicular to said third color sample index plane, and substantially perpendicular to said first color sample index plane;

b.5) said color measurement instrument optics port being between said first and third color sample index planes, and between said second and fourth color sample index planes in a position such that said color measurement instrument optics port is disposed on a distinct location on said color sample when said color sample is in juxtaposition with said first and second color sample index planes, said second and third color sample index planes, said third and fourth color sample index planes and said first and fourth color sample index planes: and b.6) said color measurement instrument optics port being also located on said color sample stage such that said color measurement instrument optics port is fully disposed on said color sample when said color sample is in juxtaposition with any pair of adjacent color sample index planes.

29. An apparatus for holding a color sample in juxtaposition with the optics shoe of a color measurement instrument comprising:

a) a color measurement instrument support plate comprising a portable color measurement instrument support surface, a color sample stage, said color sample stage defining an aperture capable of receiving the color measurement instrument optics shoe of said color measurement instrument, wherein said color measurement instrument optics shoe comprises a plane surface, and an optics port comprising a geometric center;

b) said color measurement instrument support plate secured to said color measurement instrument with said optics shoe engaged in said aperture;

c) a means for positioning said color sample in a plurality of fixed and repeatable positions on said color sample stage wherein said optics port is disposed on a distinct location on said color sample in each of said positions, and said optics port is fully covered by said color sample in all positions.

30. The apparatus of claim 29 wherein said means for positioning said color sample further comprises a substantially rectangular perimeter of said color sample stage defined by:

a) a first color sample index plane rigidly affixed to said color sample stage, and substantially perpendicular to said color sample stage;

b) a second sample index plane rigidly affixed to said color sample stage, and substantially perpendicular to said color sample stage, and substantially perpendicular to said first color sample index plane;

c) a third color sample index plane rigidly affixed to said color sample stage, and substantially perpendicular to said color sample stage, and substantially perpendicular to said second color sample index plane;

d) fourth color sample index plane rigidly affixed to said color sample stage, and substantially perpendicular to said third color sample index plane, and substantially perpendicular to said first color sample index plane;

e) said color measurement instrument optics port being between said first and third color sample index planes, and between said second and fourth color sample index planes in a position such that said color measurement instrument optics port is disposed on a distinct location on said color sample when said color sample is in juxtaposition with said first and second color sample index planes, said second and third color sample index planes, said third and fourth color sample index planes and said first and fourth color sample index planes; and f) said color measurement instrument optics port being also located on said color sample stage such that said color measurement instrument optics port is fully disposed on said color sample when said color sample is in juxtaposition with any pair of adjacent color sample index planes.

31. An apparatus for holding a color measurement instrument comprising an optics port with a geometric center, and a color sample, said apparatus comprising:

a) a color measurement instrument support plate comprising a color measurement instrument support surface, a color sample stage, and defining an aperture substantially aligned with said geometric center of said optics port;

b) a means for removably securing said color measurement instrument to said color measurement instrument support surface with said optics port substantially aligned with said aperture;

c) a means for positioning said color sample in a plurality of fixed and repeatable positions on said color sample stage wherein said optics port is disposed on a distinct location on said color sample in each of said positions, and said aperture is fully covered by said color sample in all positions; and d) a means for removably securing said color sample to said color sample stage with a uniform and repeatable force; wherein said color measurement instrument further comprises a color measurement instrument optics shoe comprising a plane surface; and said color sample stage further comprises a plane surface substantially coincident with said plane surface of said color measurement instrument optics shoe when said optics shoe is engaged in said aperture.

* * * * *